(12) United States Patent
Repka (10) Patent No.: US 7,959,904 B2
(45) Date of Patent: Jun. 14, 2011

(54) DELIVERY OF MEDICAMENTS TO THE NAIL

(75) Inventor: Michael A. Repka, Oxford, MS (US)

(73) Assignee: University of Mississippi, University, MS (US)

( * ) Notice: Subject to any disclaimer, the term of this patent is extended or adjusted under 35 U.S.C. 154(b) by 1016 days.

(21) Appl. No.: 10/830,730

(22) Filed: Apr. 22, 2004

(65) Prior Publication Data

US 2004/0197280 A1 Oct. 7, 2004

Related U.S. Application Data

(63) Continuation-in-part of application No. PCT/US02/33694, filed on Oct. 22, 2002.

(60) Provisional application No. 60/330,415, filed on Oct. 22, 2001.

(51) Int. Cl.
*A61K 31/66* (2006.01)
*A61K 31/16* (2006.01)

(52) U.S. Cl. ............ 424/61; 424/401; 424/405; 514/75; 514/784

(58) Field of Classification Search .................... 424/61, 424/401, 405
See application file for complete search history.

(56) References Cited

U.S. PATENT DOCUMENTS

| | | | |
|---|---|---|---|
| 4,180,058 A * | 12/1979 | Brem | ............................ 128/898 |
| 5,487,776 A | 1/1996 | Nimni | |
| 5,947,956 A | 9/1999 | Karell | |
| 5,993,790 A | 11/1999 | Strauss | |
| 6,042,845 A | 3/2000 | Sun et al. | |
| 6,143,794 A | 11/2000 | Chaudhuri et al. | |
| 6,224,887 B1 | 5/2001 | Samour et al. | |
| 6,231,875 B1 | 5/2001 | Sun et al. | |
| 6,264,927 B1 | 7/2001 | Monahan | |
| 6,380,236 B2 | 4/2002 | Glassman | |
| 6,391,879 B1 | 5/2002 | Reeves | |
| 6,413,555 B1 * | 7/2002 | Lee | ............................... 424/742 |
| 6,664,292 B2 * | 12/2003 | Bogart | .......................... 514/557 |
| 6,846,837 B2 | 1/2005 | Maibach et al. | |

FOREIGN PATENT DOCUMENTS

| | | |
|---|---|---|
| EP | 152281 A2 | 8/1985 |
| EP | 440298 A1 | 8/1991 |
| EP | 472858 A2 | 3/1992 |
| WO | WO08600013 A1 | 1/1986 |
| WO | WO08907930 A1 | 9/1989 |

OTHER PUBLICATIONS

Repka, M.A., O'Haver, J., See, C.-H., Gutta, K., and Munjal, M. 2002. Nail morphology studies as assessments for onychomycosis treatment modalities. *Int J Pharm* 245:25-36.

* cited by examiner

*Primary Examiner* — Gina C Yu
(74) *Attorney, Agent, or Firm* — Stites & Harbison PLLC; Richard S. Myers, Jr.

(57) ABSTRACT

The present invention includes a method for delivering a medicament to a nail plate or nail bed that comprises providing a therapeutically effective amount of a medicament, etching the surface of the nail, and applying a medicament to the surface of the nail. A preferred embodiment of the present invention is directed to a method of treating a fungal infection of the fingernail or toenail. Also included in the present invention are the compositions (i.e., the etching compositions and/or the medicament compositions) used to treat the nail in accordance with the methods of the present invention.

13 Claims, 7 Drawing Sheets

Figure 1. Atomic Force Micrograph of the human dorsal nail surface.

Figure 2. Atomic Force Micrograph of the human dorsal nail surface treated with tartaric acid 20%.

Figure 3. Atomic Force Micrograph of the human dorsal nail surface treated with phosphoric acid gel 10% (60 sec).

Figure 4. Atomic Force Micrograph of the human dorsal nail surface treated with carbomer 971P.

Figure 5. Scanning Electron Micrograph of the human nail surface (Cross-section) untreated.

Figure 6. Scanning Electron Micrograph of the human dorsal nail surface (Cross-section) treated with tartaric acid 20% (3 min).

Figure 7. Mean Roughness Values of the Dorsal Human Nail, untreated and treated as follows: Dorsal = Control (Untreated); C971 = Carbomer 971P; HPC = Hydroxypropylcellulose; TTA = Tartaric Acid; and PA = Phosphoric Acid Gel.

Figure 8. Diffusion studies of KCZ through the human dorsal nail (a) treated with phosphoric acid gel 10% for 60 sec., and (b) human dorsal nail untreated.

DELIVERY OF MEDICAMENTS TO THE NAIL

PRIORITY INFORMATION

This application is a Continuation-in-Part Application claiming priority to PCT International Application Number PCT/US02/33694 filed on Oct. 22, 2002, which claims priority to U.S. Application No. 60/330,415, filed on Oct. 22, 2001.

FIELD OF THE INVENTION

The technical field to which this invention relates includes the field of delivering medicaments to the human or animal nail. Preferred embodiments of the present invention include a composition and method for the transonychial and perionychial administration of medicaments to the human or animal nail or nail area. The present invention provides a system, method, and composition for delivering effective dosages of an active medicament or medicaments, such as antifungal agents or other antimicrobials, to penetrate the nail layers and to treat the underlying nail bed, the perionychium, or the nail itself. This penetration of the active medicaments is achieved via "etching" the nail surface to provide increased surface area for medicament penetration and absorption, in addition to increased bioadhesion for a drug delivery system.

Of course, the term "nail" is well understood in the art and includes the horny cutaneous plate on the dorsal surface of the distal end of a finger or toe. The term also applies to horny cutaneous surfaces of animals.

BACKGROUND OF THE INVENTION

1. Onychomycosis

It has been reported that at least 18% of the world population, and approximately 9% of the U.S. population, is afflicted with chronic fungal infections of the fingernails or toenails (onychomycosis). The target sites for the treatment of such infection reside in the nail plate, nail bed, and nail matrix.

Most such infections are caused by obligate aerobic fungal species, usually "dermatophytic" or yeast-like fungi, which infect the nail plate itself. Increased therapies with antineoplastic agents and a continually growing population of immunocompromised individuals, such as those infected with the Human Immunodeficiency Virus (HIV), have shown an increased incidence of systemic morbidity from this persistent disease process. Onychomycosis is a persistent fungal infection of the toenails or fingernails that is unsightly and may affect an individual's quality of life. The fungus grows on the underside of the nail, causing it to crack, become brittle, and eventually separate from the nail bed.

2. Treatment Modalities-Systemic

Historical, systemic treatment of these infections has had limited success. Furthermore, physicians are reluctant to treat what has been generally perceived as merely a cosmetic disfiguration with a systemic medication. Negative aspects associated with oral systemic antifungal therapy for onychomycosis include their limited success rate, contraindications and drug interactions, toxicity, and the high cost of the medication. Furthermore, a general movement has begun in the medical and scientific communities away from the use of systemic antimicrobial therapy because indiscriminate and widespread use of broad-spectrum antibiotics has lead to an increase in the number of resistant strains of pathogenic microorganisms.

Unfortunately, many fungal nail infections have proven to be very resistant to any type of treatment. Systemic administration of anti-fungal drugs, such as the azoles (ketoconazole, fluconazole) and the allylamines (terbinafine, butenafine), is hindered by limited blood circulation in the nail bed and poor transport to the nail plate, requiring high dosage levels for long periods of time. Such high drug dosages can have adverse side effects, and it has been found that clearance of the infection is often only temporary. Systemic treatment must often be continued indefinitely, thereby also increasing the potential for antimicrobial resistance.

3. Treatment Modalities-Topical

Topical therapy for onychomycosis is commonly thought of as the treatment of choice, since it does not lead to adverse systemic effects or drug interactions. However, topical administration of anti-fungal drugs also suffers limitations. This treatment modality has not been effective because antifungal drugs cannot readily penetrate the nail plate to reach the infection sites under the nail. The nail plate is a relatively thick structure that inhibits penetration of the drug being applied at a practical rate. Moreover, the topical application of creams, solutions, lotions and gels is often dissipated in relatively short periods of time. Although attempts have been made to incorporate topically active antifungal drugs into film-forming compositions (e.g., nail polishes or lacquers to improve drug persistence), such approaches have not proved entirely satisfactory. While removal of the nail (nail avulsion) can improve topical drug treatment, several disadvantages to this treatment modality exist which include poor patient acceptance and the ability to maintain a constant supply of the drug to the nail bed.

Although the nail is similar to the stratum corneum of the skin in that it is derived from epidermis, it is composed primarily of highly disulfide-linked keratin and is approximately 100-fold thicker than stratum corneum. The nail contains, as stated previously, three layers, with the dorsal layer being the most electron dense and resistant to antimicrobial penetration. Thus, in order to deliver a sufficient amount of drug into the nail plate, the permeability, in particular the dorsal layer, of the structure to the drug needs to be enhanced.

4. Human Nail Morphology

The nail is similar to the stratum corneum of the skin in that it is derived from epidermis, it is mainly composed of hard, relatively insoluble keratin (highly disulfide-linked); however, it is approximately 100-fold thicker than stratum corneum. The nail is convex laterally and distally in the horizontal plane and is generally regarded to have three layers: Dorsal, Intermediate and Ventral. The dorsal surface is slightly corrugated, while the ventral surface is deeply grooved for interdigitation with the nail bed, which has a rich vascular and lymphatic supply. The nail plate becomes thinner from its distal free end to its most proximal areas (thickness approx. 0.3-0.7 mm). The structure is composed of dead polyhedral shaped corneocytes, without nuclei or organelles, cemented together and filled with keratin proteins.

5. Etching

Dentistry was introduced to the acid-etch technique for tooth restoration in 1955. This idea proposed and subsequently provided for an ideal surface for bonding restorative materials to enamel using 30-40% phosphoric acid. The present inventor has applied this general principle to the nail plate. Once the nails are etched in accordance with the present invention, the development of microporosities within the nail surface (the dorsal surface, for instance) increases wettability with a resulting increase in surface area and a decrease in contact angle for the drug delivery system or the medicament.

6. Significance

Antifungal drug treatment can be effective topically treating onychomycosis after nail removal. Accordingly, there is a need for a methodology for topical nail fungal treatment that does not require removal of the nail or making holes in the nail, as is disclosed in background art (including U.S. Pat. No. 5,947,956, Karell, 1999, discussed below). The present inventor has discovered that nail avulsion or the cutting of holes is the nail is not necessary to achieve optimal drug delivery to the nail plate and the surrounding tissues.

7. Background Art

The following references represent background art with respect to the present invention, and each of the following references are hereby incorporated herein by reference in their entirety.

Olthoff et al., in EP 440298 A1, disclose the use of sulfur-containing amino acid derivatives in topical preparations for treatment of nail diseases such as onychomycosis.

Kawase et al (EP 472858 A2 Mar. 4, 1992) describe a hair treatment composition containing siloxanes and penetration enhancers such as ammonium thioglycolate, which gives the treated hair a good gloss and a reduced number of hair splits.

Puri (WO 8600013 A1 Jan. 3, 1986) discloses that the condition of hair, skin and nails is improved by treatment with an aqueous ammonium thioglycolate solution, followed by treatment with a protein hydrolyzate.

Rothman (WO 8907930 A1 Sep. 8, 1989) describes a storage-stable protein-containing composition and a method for treating keratinous tissues. The protein-containing composition contains reducing agents such as ammonium thioglycolate. The composition is said to be useful for conditioning horny keratinous tissues of mammals such as human hair and nail, and the hooves and fur of animals, to improve their strength and appearance and to promote hair and nail growth.

An enhanced transdermal drug permeation in rats has been reported for theophylline [K. Kushida et al., Chem. Pharm. Bull., 32, 1 (1984) 268-274] and insulin [Y. Sun et al., Ann. New York Academy of Sciences, 1990, 596; Y. Sun et al., Proceed. Intern. Sym. Control. Rel. Bioactive Mat., 17 (1990) 202; and J. C. Liu et al., in Drug Permeation Enhancement: Theory and Applications, p247-272, (D. S. Hsieh, Ed.) Marcel Dekker, Inc., 1994] by pretreating the skin with aqueous calcium thioglycolate solution. On the other hand, direct addition of calcium thioglycolate into an ointment containing the calcium salt of indomethacin dramatically decreased the absorption of the drug [T. Ogiso et al., J. Pharmcobio-Dyn., 9 (1986) 517-525].

Konno et. al. (EP 152281 A2 Aug. 21, 1985) describes a transdermal formulation of nicardipine hydrochloride containing urea and thioglycol.

U.S. Pat. No. 5,487,776 discloses an anti-fungal nail lacquer and method for use thereof. The anti-fungal nail lacquer contains, as an anti-fungal agent, griseofulvin. However, this invention has not been effective in treating nail infections due to permeability problems.

The ONYCHOLASER™ (previously cited, U.S. Pat. No. 5,947,956, Karell, 1999) relates generally to surgical instruments and more specifically to laser microsurgical instruments for use in cutting holes in tissues or membranes, especially the fingernails and toenails.

U.S. Pat. Nos. 6,143,794 to Chaudhuri et al.; 6,042,845 to Sun et al.; 6,380,236 to Glassman; 6,224,887 to Samour et al.; 5,993,790 to Strauss; and 6,264,927 to Monahan disclose various topical formulations for the treatment of nail fungal diseases that may be used in conjunction with the present invention.

BRIEF SUMMARY OF THE INVENTION

It is desirable to provide an effective system and composition for topically treating nail fungal infections. The present invention provides such treatment methods and compositions for delivering effective dosages of a medicament to the nail area, underlying nail bed, perionychium, or to the nail itself. The methods and compositions of the present invention may be used to treat fungal infections such as onychomycosis. Morphology studies of the nail via scanning electron and atomic force microscopy have revealed a significant change in surface topography (both qualitative and semi-quantitative) when the dorsal nail plate was subjected to the etching methods of the present invention. Additionally, the methods of the present invention provide increased permeability of a model antimycotic drug through the nail.

The benefits of the present invention are significant because, among other things, topical therapy for onychomycosis is considered by many in the field to be the treatment of choice for this disease process, since it does not lead to adverse systemic effects or drug interactions. Before the present invention, topical therapy was more difficult because of the physical properties of the nail.

The present invention includes a method for delivering a medicament to a nail plate or nail bed that comprises providing a therapeutically effective amount of a medicament, etching the surface of the nail, and applying a medicament to surface of the nail. A preferred embodiment of the present invention is directed to a method of treating a fungal infection of the fingernail or toenail.

Another embodiment of the present invention is a nail drug delivery composition that comprises an etching agent; and a therapeutically effective amount of a nail medicament. The nail medicament may be, for example, an antifungal composition.

Another embodiment of the present invention is directed to a multi-layer, bioadhesive nail medicament nail delivery system, that comprises a matrix layer and a backing layer. Generally speaking, the matrix layer comprises the medicament and the backing layer is impermeable or semi-permeable to ensure unidirectional flow of the medicaments.

The invention further includes a bandage or dressing that is adapted for the topical administration of a medicament to the nail. The bandage will generally include a flexible pad having an impervious backing with an adhesive-coated surface that is adapted to secure the pad to the nail. The pad contains a predetermined amount of a medicament.

DETAILED DESCRIPTION OF THE INVENTION

As stated above, an embodiment of the present invention is a method for delivering an active medicament to a nail plate. The delivery means includes both transonychial and perionychial delivery of the active medicament. A preferred embodiment of the present invention is directed to a method of treating a fungal infection of the fingernail or toenail.

The method of the present invention includes delivering a therapeutically effective amount of active medicament to a diseased nail plate and to the underlying nail bed, wherein the medicament absorption can be increased by first (or concurrently) "etching" the nail surface (usually the dorsal surface) to increase surface area and thus increase drug permeability. Consequently the surrounding skin tissues, including nail bed and matrix via the eponychium and hyponychium, receive the active medicament at an effective rate due to the increased penetration of the active medicament, or by the increased bioadhesion of a delivery device to the surrounding tissues. Preferably, the medicament comprises an antifungal compound.

Etching

The medicament delivery process can be achieved via chemical or mechanical etching of the nail surface prior to or during application of the drug delivery system (i.e., the active medicament). The etching is performed to increase the surface area of the nail, which provides an increase in the permeation of the medicament, while in addition providing an increased and more consistent surface area to allow for bioadhesion of a drug delivery system or device.

The etching of this method may be performed chemically with agents such as, but not limited to, inorganic or organic acids, or by mechanical means such as, but not limited to, an etching instrument (such as a laser) or other effective device to alter the surface of the nail that would achieve the purposes of the present invention (i.e., a mini-sandblaster). For example, the microsurgical laser unit of Karrell, U.S. Pat. No. 5,947,956, incorporated herein by reference, may be used in the etching step of the methods of the present invention.

Optionally a nail priming technique may be performed during or before the etching step of the method of the present invention. Acceptable primers include dental primers that are used to create better bonding or bioadhesion while etching teeth and applying filling materials. These agents are known to those skilled in the art. Examples of these priming agents include, but are not limited to, maleic and itaconic acid. This invention includes self-etching primers, such as the two organic acids listed above, that allow for the bonding of a drug delivery system and the resulting delivery of the system's medicaments to the nail and/or the perionychium.

In certain embodiments of the present invention, the etching may be performed chemically by etching agents in an etching agent composition. Etching agents of the present invention include, for example, inorganic acids such as phosphoric acids and organic acids such as carboxylic acids and more specifically, tartaric acids. The etching agents may be present in the composition in amounts ranging from about 0.01% to about 95%, preferably in amounts ranging from about 1% to about 40%. Preferred etching agents are tartaric acid and phosphoric acid. Most preferably the tartaric acid is present in an amount of about 20%, and the phosphoric acid is present in an amount of about 10%.

The etching agent of the present invention may further comprise a nail medicament. Examples of the nail medicaments include at least one of the following: antifungal or antimicrobial agents, nail growth agents, nail hardening agents, and nail softening agents. Alternatively, at least one of the medicaments listed above (as well as other possible nail medicaments not part of the above list) can be applied to the nail and nail area as a separate medicament composition after the etching process.

The etching agents of the present invention may include the primers listed above. Also, the etching agents can be applied after the primers are applied to the nail.

These aforementioned etching and other agents are to be administered in an amount sufficient to assist enhancement of the permeation of the antifungal or antimicrobial drugs or other medicaments to or through the nail tissue, and/or perionychium, with optimal bioadhesion.

Preferably, after etching, the nail surface will experience an increase in surface area in terms of roughness of from about at least 10% to about at least 10000%. More preferably, the roughness or surface area increases at least 20%.

Further, the nail may be filed using mechanical means, such as a nail file, for example, to reduce nail thickness and provide a more appropriate contour of the infected nail. This optional step may be especially beneficial for toenails.

Penetration Enhancers

Penetration enhancers, or keratolytic agents, known in the art, may be used in a composition of the present invention or as part of the methods of the present invention to assist in the delivery of the active medicament to the nail plate and surrounding tissues.

Without being bound by theory, a keratolytic agent, i.e., a desquamating agent, helps loosen keratin in the nail and aids in the process of desquamation or the removal of the upper layers of the damaged or diseased nail. Examples of keratolytic agents include urea, benzoylperoxide, salicylic acid, resorcinol, tretinoin, and others that may be found in "Remington: The Science and Practice of Pharmacy, Nineteenth Edition, pp. 878-879. The optional keratolytic agent will be present in an amount of about 0.01% wt. to about 25% wt., preferably about 0.5% wt. to about 20% wt., more preferably about 1% wt. to about 20% wt.

The preferred penetration enhancers are those known in the art for use with onychomycosis medications. For example, ammonium thioglycolate (see EP 472858) may be used. The most preferred penetration enhancers are urea, sodium sulfide and ammonium thioglycolate.

Medicaments

The etching agent may comprise at least one nail medicament. Optionally the medicament may be applied as a separate medicament and/or as part of a separate step in the method of the present invention.

When used herein, the term medicament is understood to include at least one nail medicament or, optionally, a pharmaceutically acceptable salt thereof. The term "pharmaceutically-acceptable" salt means a salt of an active compound that retains the biological effectiveness of the compound and that is not pharmacologically undesirable. A pharmaceutically-acceptable acid addition salt is one prepared from an organic or inorganic acid that pairs with an appropriate base, e.g., an amino group in the active compound. Inorganic salts derived are from inorganic acids such as hydrochloric acid, hydrobromic acid, sulfuric acid, nitric acid, phosphoric acid and the like. Organic salts are derived from acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, lactic acid and the like.

Additionally, it is understood that the amount, when present in a composition or part of a method, is a therapeutically effective amount.

The preferred medicament of the present invention is one that comprises a therapeutically effective amount of an antifungal compound.

The antifungal drugs that can be used in the invention include miconazole nitrate, ketoconazole, itraconazole, fluconazole, econazole, terconazole, saperconazole, amorolfine, ciclopirox, oxiconazole, clotrimazole, terbinafine, butenafine, naftifine, and other antifungal drugs that are available in a topical formulation. The preferred antifungal drugs for use in the process of the invention are itraconazole, ketoconazole, fluconazole, terbinafine and butenafine.

If desired, the topical formulation containing the antifungal drug may include an agent such as hydroxypropyl-.beta.-cyclodextrin that enhances the water-solubility of the antifungal drug, in order to better utilize the aqueous pathway through the nail, as discussed above.

The antifungal formulations of the present invention include those listed in U.S. Pat. Nos. 6,143,794 to Chaudhuri et al.; 6,042,845 to Sun et al.; 6,380,236 to Glassman; 6,224,887 to Samour et al.; 5,993,790 to Strauss; and 6,264,927 to Monahan.

The antifungal compound useful in this invention is one that is effective when applied topically to treat the fungal infection. The amount of the compound present in the composition will be the amount that is therapeutically effective, i.e. an amount that will result in the effective treatment of the onychomycosis when applied in accordance with the instructions described herein.

Further, the term "treatment" covers any treatment of onychomycosis in a mammal, particularly a human, and includes:

(i) preventing the disease from occurring in a subject which may be predisposed to the disease but has not yet been diagnosed as having it;

(ii) inhibiting the disease, i.e. arresting its development; and (iii) relieving the disease, i.e. causing regression of the disease.

The therapeutically effective amount will vary depending on the subject and the severity of the affliction and may be determined routinely by one of ordinary skill in the art in light of the teaching herein. Generally, a therapeutically effective amount will be from about 0.1% (wt.) to about 40% (wt.) based on the total final weight of the composition. Preferably, the amount will be about 0.5% to about 20% by weight and more preferably about 1% to about 10% by weight.

In some embodiments, the composition is a liquid or semi-solid, such as a cream, ointment, lotion, lacquer, or gel (preferably a gel) having a solvent in which the antifungal compound (or other nail medicament, when used), or its salt, is dissolved. Thus, the composition will contain at least the antifungal compound, a solvent for the compound, and a gelling agent. Preferably, the composition is water-based, which means that the solvent is preferably water-miscible. In addition, the composition may include a surfactant to aid in the delivery of the antifungal through the nailplate; a film-forming agent; a buffering agent to adjust the pH of the composition; and an adherence-promoting agent to assist in adhering the composition to the nailplate. The composition may be applied directly to the nail or applied in an absorbent pad. Examples of a lacquer of the present invention include the formulations disclosed in U.S. Pat. No. 5,487,776 in combination with the etching agent of the present invention. Further, the present invention includes the nail medicament formulations in combination with the etching agent of the present invention.

Bioadhesive agents may be used to increase the retention and thus the effectiveness of the drug delivery system or medicament. These agents may include a polycarbophil, a carbomer or other bioadhesive agent known to those skilled in the art, such as chitosan or carboxymethyl cellulose. These agents may be incorporated at 0.1 to 25%. Preferably at 1% to 10%.

Additional/Optional Medicaments for Use with Methods of the Invention

In other embodiments of the present invention, the composition may include medicaments that are traditionally used to treat the nail. These medicaments may include those that are used to soften nails, increase growth of nails, or treat cracked nails. The etching delivery methods of the present invention may be used to deliver these traditional medicaments, either alone or in a combination of medicaments that may or may not include fungal medicaments. Example include urea, sodium sulfide, glycerin and ammonium thioglycolate, to name a few.

As stated above, an embodiment of the present invention includes a method for delivering a medicament to a nail plate or nail bed that comprises providing a therapeutically effective amount of a medicament, etching the surface of the nail, and applying a medicament to surface of the nail. This comprises the transonychial or perionychial administration to and around the nail and if desired, to the surrounding skin. Further, any known medicament composition or formulation may be used as the medicament composition or medicament/etching composition of the present invention.

With respect to applying the medicament to the surface of the nail, any know method of delivering medicaments may be used. For example, see U.S. Pat. Nos. 6,143,794 to Chaudhuri et al.; 6,042,845 to Sun et al.; 6,380,236 to Glassman; 6,224,887 to Samour et al.; 5,993,790 to Strauss; and 6,264,927 to Monahan.

The "etching" of the nail plate may occur either prior to or concurrently with the transonychial or perionychial administration to the nail of an effective amount of the medicament. These methods specifically include the application of antifungal or other antimicrobial agents or medicaments to treat the nail and immediate nail area.

The compositions of the present inventions may optionally comprise a bioadhesive agent to enhance permeation of the nail medicament.

Another embodiment of the present invention includes a film (pre-formed or in situ) delivery system adapted for the transonychial or perionychial administration of medication to the nail. This embodiment comprises a predetermined (gel, liquid or film "patch") or custom trimmed device composed of single or multiple layers. One of the layers should be a bioadhesive layer or contain within the matrix layer, a bioadhesive. Another said layer should be an etching layer or contain within the matrix layer, the etching agent, such as a carboxylic or other acid. The matrix layer may contain a nail medicament discussed above such as an antifungal or antimicrobial drug or drugs, penetration enhancing or keratolytic agents, and/or may be utilized as a rate controlling membrane. In this embodiment the film preferably includes an impermeable or semi-permeable backing layer to ensure unidirectional flow of the active medicaments, which covers the drug-containing layer. This system should be adhered to the surface of the nail to allow for penetration and/or absorption of the antifungal or antimicrobials drugs to the nail and perionychium.

This embodiment may use the hot-melt extrusion technology for the production of thin, flexible acrylic films for topical drug delivery as described by Aitken-Nichol et al., Pharm Res 13: 804-808 (1996), the contents of which are incorporated herein by reference. Also see reference numbers 30-38, below. The active compound may be embedded in a carrier formulation comprised of one or more meltable substances or other functional excipients. The meltable substance may be polymeric materials or low melting point waxes. The bioavailability of the drug substance could be improved when it is dispersed at the molecular level in hot-melt extruded dosage forms. Also see references 39-41.

The film systems of this embodiment may be also be produced by their being cast from organic or aqueous solvents with a casting method known in the art.

Hydroxypropyl cellulose (HPC) and poly(ethylene oxide) (PEO) may be utilized as polymeric carriers for the matrix film formulations. Medicaments may be incorporated into the film in effective amounts. Preferred are antifungal compounds and compositions. Most preferred are ketoconazole and terbinafine or butenafine, which may be incorporated in the films at amounts ranging from about 0.1% to about 40%, preferably about 20% (w/w). Polycarbophil (Noveon® AA-1) may be incorporated as a bioadhesive and polyethylene glycol (PEG 3350) as a plasticizer. Butylated hydroxytoluene (BHT) and propyl gallate may be utilized as antioxidants. Propyl gallate has also been reported to exhibit antifungal properties in addition to its potential synergistic effect with BHT.

Prior to the hot-melt extrusion process, all of the ingredients in the formulation are blended and dried to minimize moisture content. The formulations may then be fed into the hopper and transferred inside the heated barrel by the rotating extruder screw which may be extruded into thin films utilizing a Killion Model KLB-100 extruder equipped with a 6 inch flex-lip die (preferred thickness of the film being about 0.3-1.0 mm). The films may then be collected in rolls, labeled and sealed in foil-lined 5-mil polyethylene bags (1 mil=25.4 μm or 0.001 inch). The extrusion temperatures will be dependent on the polymeric carriers utilized in the drug delivery system. Screw speed of about 70-80 rpm is preferred (approximate barrel residence time of 90 seconds) for this type of extruder.

The compositions of the present invention may be incorporated into a bandage or dressing adapted for topical administration of the composition to the nail. The compositions may be incorporated in a flexible pad of an adhesive bandage.

In other embodiments, the etching methods of the present invention can be used as part of an improved method of applying false (acrylic or other appropriate materials) to fingernails or toenails. In these embodiments, the surface of the nail may be etched according to the present invention, and subsequent to etching false fingernail material can be applied to the nail for nail lengthening or improving nail appearance. These methods increase the retention time and integrity of the false nail so that they may be less likely to be separated from the human/animal nail. Additionally, the false fingernail material (acrylic or other appropriate materials) may contain one or more medicaments. The medicament may be at least one of an antifungal agent, to nail growth agent, nail hardening agent, nail softening agent, nail penetration enhancer antimicrobial agent, keratolytic agent or a bioadhesive agent.

The antifungal material may be applied after the etching step via an appropriate composition (solution, film, etc.) followed by the applying of the false nail material.

EXAMPLES

The best mode for carrying out the invention as contemplated by the Applicant at the time of filing this Application is evident from the Examples listed below.

The following examples serve only to illustrate the present invention. They are representative in nature and should not by construed in any way as narrowing or limiting the scope of the invention as claimed.

Example 1

After etching the dorsal surface of the nail with a 10% phosphoric acid, carbomer hydroalcoholic gel, the following hot-melt extruded composition is applied to the nail:

| Drug/Chemical (% w/w) | Antifungal Composition |
|---|---|
| Hydroxypropyl cellulose (Avg MW: 850,000) | 41.23 |
| Hydroxypropyl cellulose (Avg MW: 350,000) | 12 |
| Polyethylene Oxide (Avg MW: 200,000) | 20.5 |
| Propylparaben NF | 0.02 |
| Methylparaben NF | 0.20 |
| Butylated Hydroxytoluene NF | 0.05 |
| Polycarbophil (Noveon AA-1) | 4.00 |
| Tartaric Acid | 2.0 |
| Polyethylene glycol 3350 | 10.0 |
| Ketoconazole, USP | 10.0 |

Example 2

Example 2 is an in situ film formulation for the etching and concomitant nail softening nail composition.

| Drug/Chemical (% w/w) | Etching/Nail Softener |
|---|---|
| Hydroxypropyl cellulose (Avg MW: 80,000) | 21.78 |
| Polyethylene glycol 3350 | 15 |
| Ethanol (95%) | 30 |
| Propylparaben NF | 0.02 |
| Methylparaben NF | 0.20 |
| Urea | 10 |
| Carbomer 971P | 3.9 |
| Lactic Acid | 4.0 |
| Triethanolamine (TEA) | 0.1 |
| Purified Water | 15.0 |

Example 3

Figure 1:
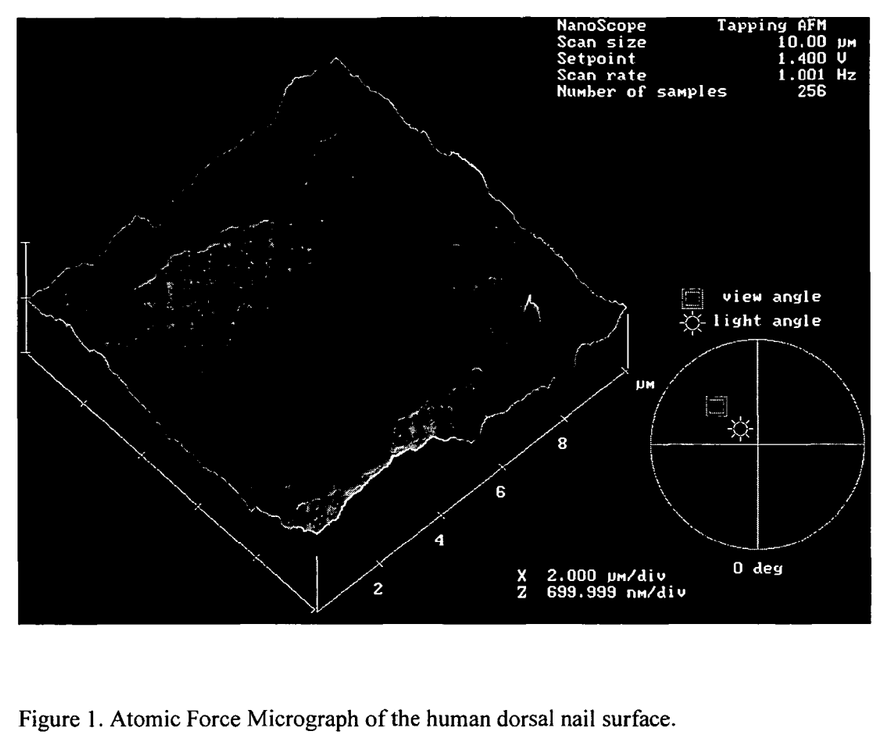
FIG. 1 is an Atomic Force Micrograph of the human dorsal nail surface.
Figure 2:
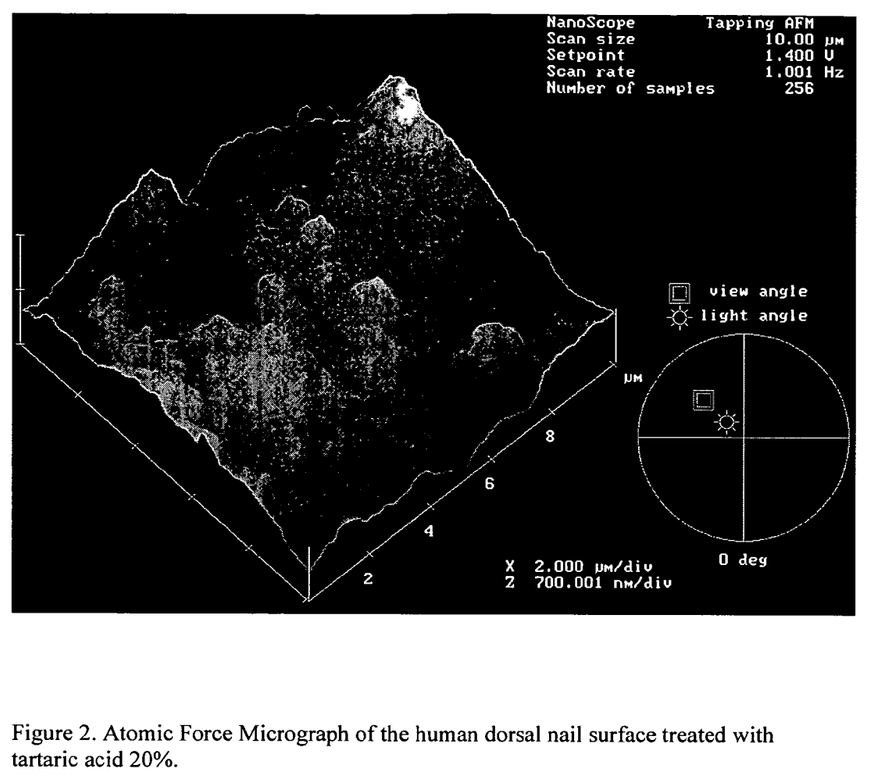
FIG. 2 is an Atomic Force Micrograph of the human dorsal nail surface that has been treated with tartaric acid (20%).
Figure 3:
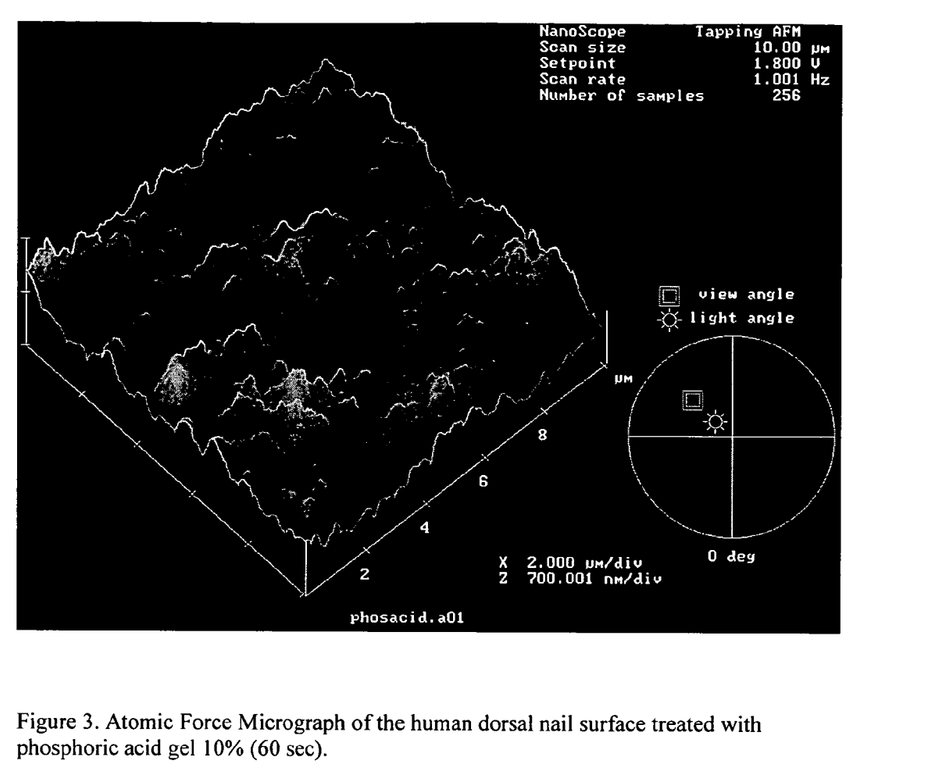
FIG. 3 is an Atomic Force Micrograph of the human dorsal nail surface that has been treated with phosphoric acid gel (10%) (60 sec).
Figure 4:
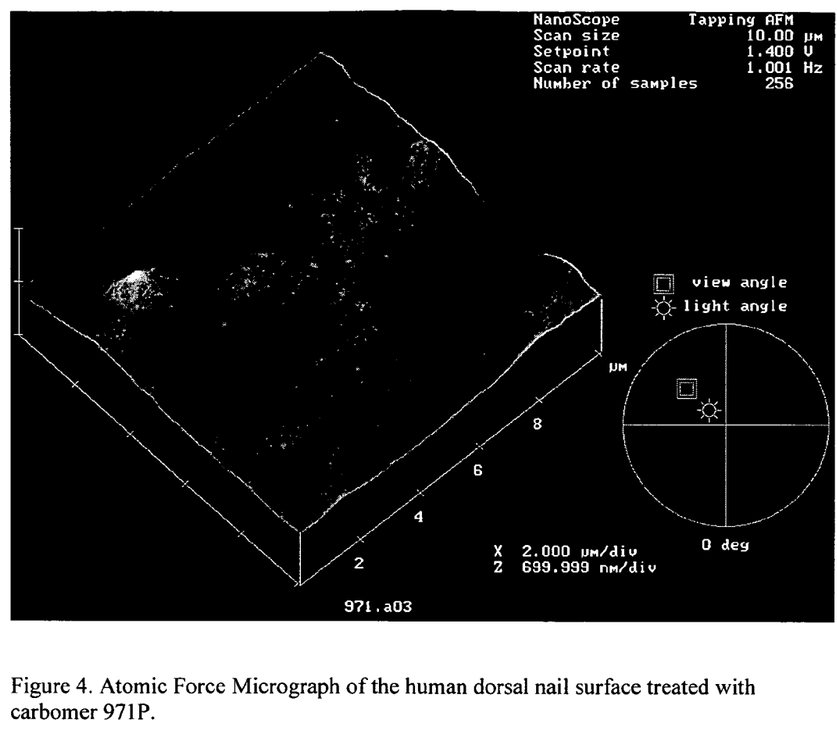
FIG. 4 is an Atomic Force Micrograph of the human dorsal nail surface that has been treated with carbomer 971P.
Figure 5:
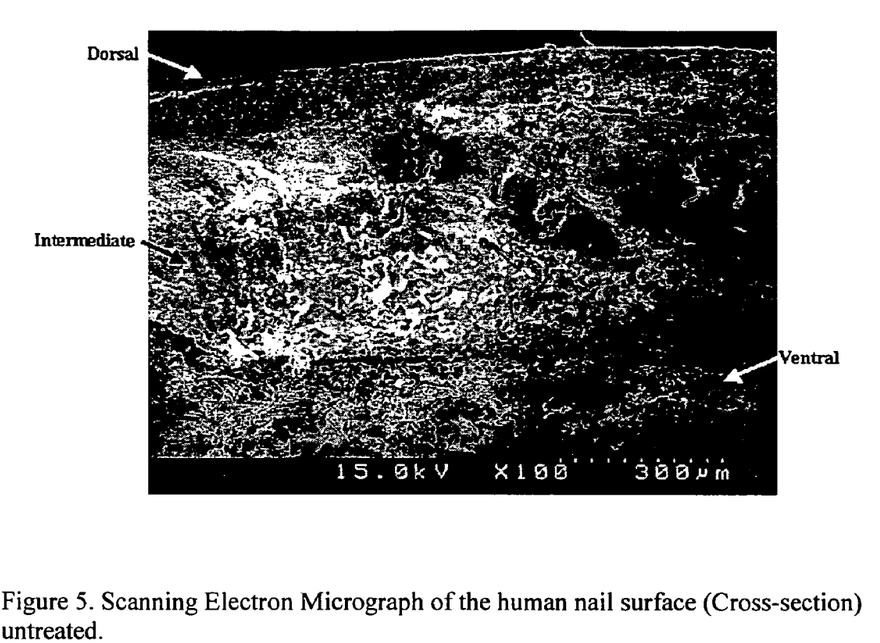
FIG. 5 is a Scanning Electron Micrograph of the human nail surface (cross-section) untreated.
Figure 6:
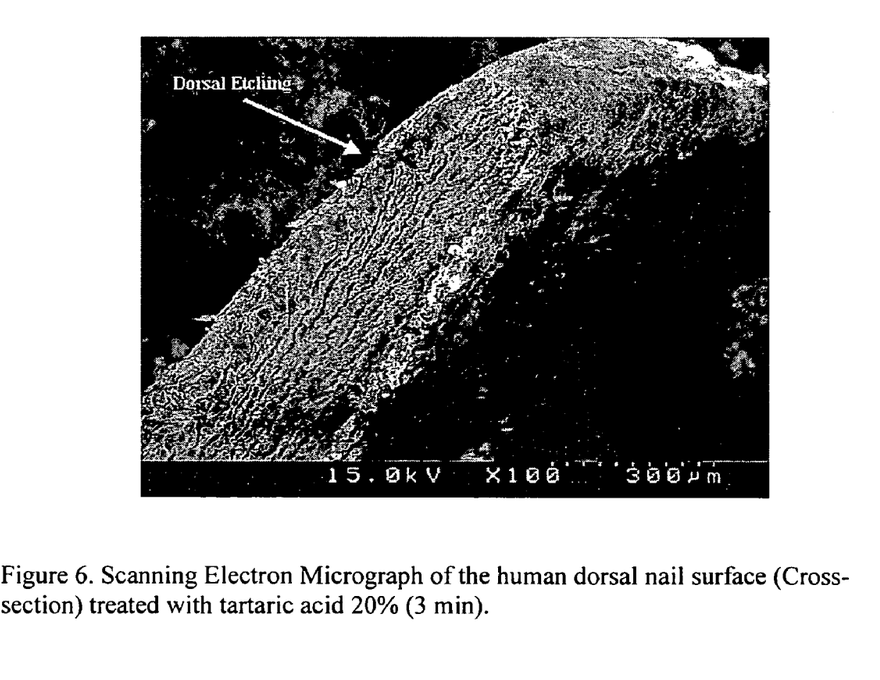
FIG. 6 is a Scanning Electron Micrograph of the human dorsal nail surface (cross-section) treated with tartaric acid (20%) (3 min).
Figure 7:
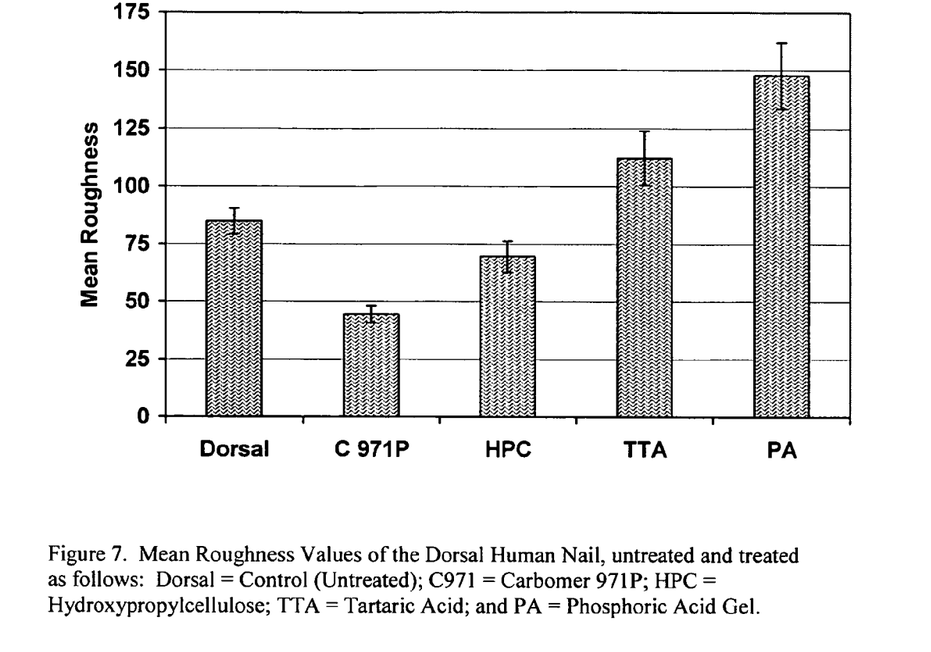
FIG. 7 is a chart demonstrating the Mean Roughness Values of the dorsal human nail, untreated and treated as follows: Dorsal=control (untreated); C971=Carbomer 971P; HPC=Hydroxypropylcellulose; TTA=Tartaric Acid; and PA=Phosphoric Acid Gel.

Example 3 is an example of chemically etching a human nail and examining the etched nail's morphology. In this example, a 20% tartaric acid (TTA) solution is applied to human nail samples for 120 seconds as a chemical etching agent. Atomic Force Microscopy (AFM), scanning electron microscopy (SEM), and polarized light microscopy (PLM) were utilized to visualize nail morphology and topographical changes in the nail samples subject to the chemical agent. A review of the AFM micrographs reveal significant changes in topography to the dorsal layer as a result of the chemical agent being applied. Roughness scores, as determined by Nanoscope™ IIIa software, recorded a significant change in surface roughness of the etched nail when compared to the control (no treatment) (112.2 vs. 85.0 nm, respectfully). See FIG. 7.

Example 4

Example 3 is repeated, but with human nail samples treated with a phosphoric acid (10%) gel for 60 seconds. The roughness increase is about two-fold greater vs. the control (147.8 vs. 85.0 nm, respectfully). See FIG. 7.

Example 5

Example 5 examines bioadhesion, and demonstrates determining and comparing the bioadhesive properties of hot-melt extruded polymeric film systems for onychomycosis on the human nail not treated and treated with a surface etching method of the present invention. The film systems containing the antifungal medicament ketoconazole are prepared using a single screw Killion extruder (KLB-100). The film has the following content:

| Drug/Chemical (% w/w) | Antifungal Composition |
|---|---|
| Hydroxypropyl cellulose (Avg MW: 850,000) | 36.23 |
| Hydroxypropyl cellulose (Avg MW: 350,000) | 18 |
| Polyethylene Oxide (Avg MW: 200,000) | 23.5 |
| Propylparaben NF | 0.02 |
| Methylparaben NF | 0.20 |
| Butylated Hydroxytoluene NF | 0.05 |
| Polycarbophil (Noveon AA-1) | 5.00 |
| Tartaric Acid | 2.0 |
| Polyethylene glycol 3350 | 5.0 |
| Ketoconazole, USP | 10.0 |

The extruded films are applied to human nail samples, in-vitro. Tensile and peel tests of the film are performed on the nail substrates using a Texture Analyzer® (TA.XT2i) equipped with Texture Expert® Software. Bioadhesive profiles of the films are determined from the recorded data. The instrument variables used were contact time and speed of withdrawal of the probe from the tissue. The nail samples tested are either non-treated (control) or treated with phosphoric acid gel 10% (PA), a chemical etching agent of the present invention. Peak adhesion force (PAF) and area under curve (AUC) are determined for the bioadhesion testing.

PAF and AUC are determined to be greater for human nail samples treated with the PA gel compared to that of the control for each of the instrument variables studied. Utilizing the peel test, (contact time of 10 seconds), the PAF and AUC are 3.9 N and 3.9 mJ respectively, for the treated samples compared to that of the control (1.6 N and 2.6 mJ). In addition the tensile test resulted in a PAF of 4.1 N for the control vs. 5.6 N for the PA treated nail. Without being bound by theory, the greater peak force and AUC recorded for the etched nail to the film is a result of the microporosity and increased surface area that allows for more effective polymer chain interdiffusion. The nail samples treated in accordance with the present invention increase PAF and AUC values of both peel and tensile tests compared to that of the untreated nail.

Example 6

Example 6 examines permeability of the medicament into the nail. For this Example, ketoconazole is utilized as a model drug to perform permeability studies. The drug is dissolved in two different media for testing which functioned as the donor solution. The first is an isotonic phosphate buffer solution (pH 7.2) with 0.5% Brij 58 as a solubilizer. The second is an 80:20 methanol/water solution buffered to pH 7.2. The receptor media is the same as the donor media without dissolved drug in both cases.

A system employing 9 modified glass Franz diffusion cells is used. Full thickness nail plates are sandwiched between two polypropylene adapters with an O-ring and were mounted on the individual cells with the dorsal nail plate facing the donor compartment (receptor volume 5.2 ml; donor surface area 0.5 $cm^2$). The receptor fluid is maintained at 37±0.5° C. and is continuously stirred with a magnetic bar. The donor solutions are applied to the dorsal nail surface following a one hour hydration period. Samples of the receptor phase are withdrawn at predetermined time intervals (for up to 48 hours) and immediately replaced with fresh donor solution. Analysis of the samples is corrected for previous drug removed. The receptor and donor compartments are sealed with a sheet of aluminum foil and wrapped with parafilm. The hermeticity of the system was continuously monitored. Drug content in the receptor media is determined using high performance liquid chromatography.

Figure 8:
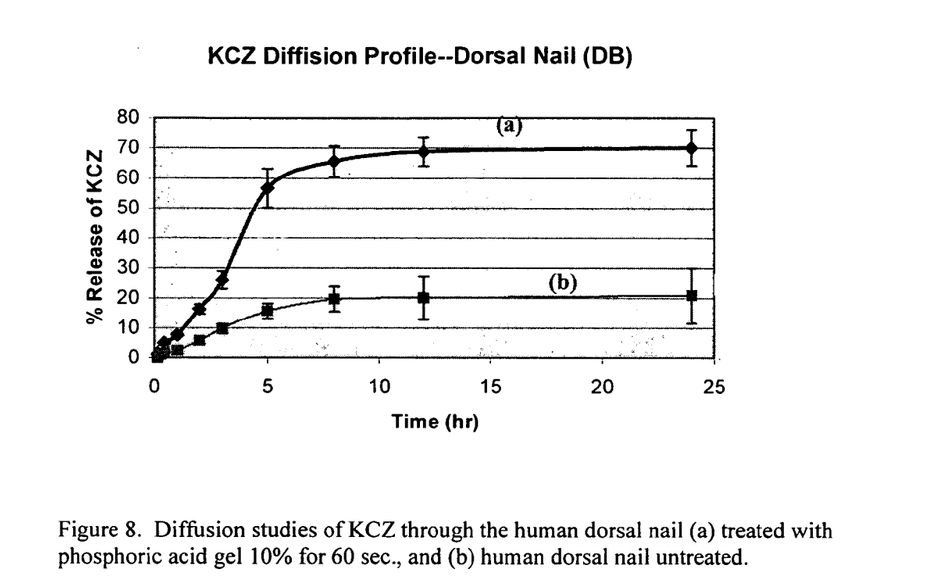
FIG. 8 is a chart demonstrating diffusion studies of KCZ through the human dorsal nail (a) treated with phosphoric acid gel 10% for 60 sec., and (b) human dorsal nail untreated.

The ketoconazole (phosphate buffer/Brij 58) that permeats the unetched nail plates after 48 hours is 446 (±51) $\mu g/cm^2$. However, total permeation of drug through the etched nail plates after the same time interval is 1,873 (±155) $\mu g/cm^2$, or approximately a 4-fold difference. The same directional difference is recorded with the buffered methanol/water solution of ketoconazole. The nail etched in accordance with the present invention exhibits an approximate 3-fold greater total permeation of drug (6,191±323.3 $\mu g/cm^2$) than that of the nonetched nail (2,497±237 $\mu g/cm^2$). Also, see FIG. 8.

Example 7

A phosphoric acid carbomer, hydroalcoholic gel at 10%, is applied to the dorsal nail surface for 60 seconds, then washed for 1 minute with approximately 100 ml of purified water and air dried at room temperature for approximately 5 minutes. Afterward, a composition of Example 1 is applied to the nail with light pressure until the film system was not tacky to touch. The film delivery system is then left on the nail for a period of 48 hours.

REFERENCES

1. Wessel, S. et al., Hydration of human nails investigated by NIR-FT-Raman spectroscopy. *Biochimica et Biophysica Acta* 1433:210-216 (1999).
2. Kobayashi, Y., Miyamoto, M., Sugibayashi, K., and Morimoto, Y. 1999. Drug permeation through the three layers of the human nail plate. *J Pharm Pharmacol* 51:271-278.

3. Gniadecka, O. F., Nielsen, D. H., Christensen, H. C., and Wulf, H. C. 1998. Structure of water, proteins, and lipids in intact human skin, hair and nail. *J Investigative Derm* 202:393-398.
4. Bertram, J. E. A., and Gosline, J. M. 1987. Functional design of horse hoof keratin the modulation of mechanical properties through hydration effects. *J. Exp. Biol.* 130:121-136.
5. Fraser, R. D. B., and Macrae, T. P. 1980. Molecular structure and mechanical properties of keratins. In *Symposia of the Society for Experimental Biology*. Cambridge: Cambridge University Press. 211-257.
6. Marshall, R. C. 1983. Characterization of the protein of human hair and nail by electrophoresis. *J. Invest. Dermatol.* 80:519-524.
7. Baden, H. P., and Laurence, B. 1968. The a-fibrous proteins of epidermis. *J. Invest. Dermatol.* 51:478-483.
8. Baden, H. P., and Kvedar, J. C. 1991. The Nail. In *Physiology, Biochemistry, and Molecular Biology of the Skin*. L. A. Goldsmith, editor. Oxford: Oxford University Press. 697-711.
9. Quintanar-Guerrero, D. 1998. The effect of keratolytic agents on the permeability of three imidazole antimycotic drugs through the human nail. *Drug Dev Ind Pharm* 24.
10. Gupta, A. K., and Scher, R. K. 1998. Oral antifungal agents for onychomycosis. *Lancet* 351:541-542.
11. Scher, R. K. 1996. Onychomycosis: a significant medical disorder. *J Am Acad Dermatol* 35: S2-5.
12. Schlefman, B. S. 1999. Onychomycosis: a compendium of facts and a clinical experience. *J Foot Ankle Surg* 38:290-302.
13. Niewerth, M., and Korting, H. C. 1999. Management of onychomycosis. *Drugs* 58:283-296.
14. Piraccini, B. M., and Tosti, A. 1999. Drug induced nail disorders: incidence, management and prognosis. *Dur Saf* 21:187-201.
15. Tom, C. M., and Kane, M. P. 1999. Management of toenail onychomycosis. *Am J Health Syst Pharm* 56:865-871.
16. Tosti, A., Baran, R., and Piraccini, B. M. 1999. 'Endonyx' Onychomycosis: a new modality of nail invasion by dermatophytes. *Acta Derm Venereol* 79:52-53.
17. Debruyne, D., and Coquerel, A. 2001. Pharmacokinetics of Antifungal Agents in Onychomycosis. *Clin Pharmacokinet* 40:441-472.
18. Scher, R. K. 1999. Onychomycosis: therapeutic update. *J Am Acad Dermatol* 40: S21-26.
19. Whittam, L. R., and Hay, R. J. 1997. The impact of onychomycosis on quality of life. *Clin Exp Dermatol* 22:87-89.
20. Lubeck, D. P., Patrick, D. L., McNulty, P., Fifer, S. K., and Birnbaum, J. 1993. Quality of life of persons with onychomycosis. *Qual Life Res* 2:341-348.
21. Evans, E. G. 1998. Causative pathogens in onychomycosis and the possibility of treatment resistance: a review. *J Am Acad Dermatol* 38:S32-56.
22. Walters, K. A., Flynn, G. L., and Marvel, J. R. 1983. Physicochemical characterization of the human nail: permeation pattern for water and the homologous alcohols and differences with respect to the stratum corneum. *J Pharm Pharmacol* 35:28-33.
23. Buonocore, M. G. 1955. A simple method of increasing the adhesion of acrylic filling materials to enamel surfaces. *J Dent Res* 34:849-853.
24. Retief, D. H. 1973. Effect of conditioning the enamel surface with phosphoric acid. *J Dent Res* 52:333-341.
25. Perdigao, J., Frankenberger, R., Rosa, B. T., and Breschi, L. 2000. New trends in dentin/enamel adhesion. *Am J Dent* 13:25-30.
26. Manson-Rahemtulla, B., Retief, D. H., and Jamison, H. C. 1984. Effect of concentrations of phosphoric acid on enamel dissolution. *J Prosthet Dent* 51:495-498.
27. 1998. Prompt L-Pop Compomer Adhesive. In *Product Dossier ESPE GmbH*. Seefeld, Germany.
28. 1998. NRC Non-rinse Conditioner. In *Technical Manual Dentsply DeTrey*. Konstanz, Germany.
29. Aitken-Nichol, C., Zhang, F., and McGinity, J. W. 1996. Hot melt extrusion of acrylic films. *Pharm Res* 13:804-808.
30. Follonier, N., Doelker, E., and Cole, E. T. 1994. Evaluation of hot-melt extrusion as a new technique for the production of polymer-based pellets for sustained release capsules containing high loadings of freely soluble drugs. *Drug Dev Ind Pharm* 20:1323-1339.
31. Follonier, N., Doelker, E., and Cole, E. T. 1995. Various ways of modulating the release of diltiazem hydrochloride from hot-melt extruded sustained release pellets prepared using polymeric materials. *J Controlled Release* 36:243-250.
32. Grunhagen, H. H., and Muller, O. 1995. Melt extrusion technology. *Pharmaceutical Manufacturing International*: 166-170.
33. McGinity, J. W., Zhang, F., Repka, M. A., and Koleng, J. J. 2000. Thermal Processing of Pharmaceutical Powders. *Pharm. Tech. Japan* 16:897-913.
34. Repka, M. A., and McGinity, J. W. 2000. Physical-mechanical, moisture absorption and bioadhesive properties of hydroxypropylcellulose hot-melt extruded films. *Biomaterials* 21:1509-1517.
35. Repka, M. A., and McGinity, J. W. 2000. Influence of Vitamin E TPGS on the properties of hydrophilic films produced by hot-melt extrusion. *Int J Pharm* 202:63-70.
36 Repka, M. A., and McGinity, J. W. 2001. Bioadhesive Properties of Hydroxypropylcellulose Topical Films Produced by Hot-Melt Extrusion. *J Control Release* 70:341-351.
37. Repka, M. A., and McGinity, J. W. 2001. Influence of Chlorpheniramine Maleate on Topical Films Produced by Hot-Melt Extrusion. *Pharm Dev Tech* 6:295-302.
38. Repka, M. A., McGinity, J. W., Zhang, F., and Koleng, J. J. 2001. Hot-Melt Extrusion Technology. In *Encyclopedia of pharmaceutical Technology*. J. Swarbrick, and J. Boylan, editors. New York: Marcel Dekker.
39. Repka, M. A., Gerding, T. G., Repka, S. L., and McGinity, J. W. 1999. Influence of plasticizers and drugs on the physical-mechanical properties of hydroxypropylcellulose films prepared by hot-melt extrusion. *Drug Dev Ind Pharm* 25:625-633.
40. Zhang, F., and McGinity, J. W. 1999. Properties of sustained-release tablets prepared by hot-melt extrusion. *Pharm. Dev. Technol.* 4:241-250.
41. Sato, H., and Miyagawa, Y. 1997. Dissolution Mechanism of Diclofenac Sodium Wax Matrix Granules. *J Pharm Sci* 86:929-934.
42. Thorndike, E. E. 1968. A microscopic study of the marmoset claw and nail. *Am. J. Phys. Anthropol.* 28:247-261.
43. Montagna, W., and Parakkal, P. F. 1974. *Nails in the structure and function of skin*. New York: Academic Press.
44. Mauro, J., Lumpkin, L. R., and Dantzig, P. I. 1975. Scanning electron microscopy of psoriatic nail pits. *NY State J. Med.* 75:339-342.

45. Germann, H., Barran, W., and Plewig, G. 1980. Morphology of corneocytes from human nail plates. *J. Invest. Dermatol.* 74:115-118.
46. Baden, H. P., and Kibilus, J. 1984. A comparative study of the immunologic properties of hoof and nail fibrous proteins. *J. Invest. Dermatol.* 83:327-331.
47. Baden, H. P. 1987. The Nail. In *Diseases of the hair and nail*: Year Book Medical Publishers.
48. Repka, M. A., O'Haver, J., See, C.-H., Gutta, K., and Munjal, M. 2002. Nail morphology studies as assessments for onychomycosis treatment modalities. *Int J Pharm* 245: 25-36.
49. Song, Y., Li, S. K., Peck, K. D., Zhu, H., Ghanem, A. H., and Higuchi, W. I. 2002. Human epidermal membrane constant conductance iontophoresis: alternating current to obtain reproducible enhanced permeation and reduced lag times of a nonionic polar permeant. *Int J Pharm* 232:45-57.
50. Rowe, R. C. 1980. Rate effects in the measurement of the adhesions of film coatings to tablet surfaces. *J Pharm Pharmacol* 32:214-215.
51. Repka, M. A., Prodduturi, S., and Stodghill, S. P. 2002. Production and characterization of hot-melt extruded films containing clotrimazole. *Drug Dev Ind Pharm* Submitted September 2002.
52. Weller, P. J. 2000. Propyl gallate. In *Handbook of Pharmaceutical Excipients*. K. H. Arthur, editor. Washington, D. C.: American Pharmaceutical Association. 447-449.
53. Chen, X., Young, T. J., Sarkari, M., Williams, R. O., and Johnston, K. P. 2002. Preparation of cyclosporin A nanoparticles by evaporative precipitation into aqueous solution. *Int J Pharm* 242:3-14.

Throughout the disclosure, various publications are referenced, including those in the section above. All such publications are expressly incorporated herein by reference in their entirety.

The invention thus being described, it would be obvious to one of ordinary skill in the art that the same may be varied in many ways. Such variations are not to be regarded as a departure from the spirit and scope of the present invention, and all such modifications as would be obvious to one of ordinary skill in the art are intended to be included within the scope of this invention.

I claim:

1. A method for delivering a medicament to a nail plate or nail bed, comprising:
   (1) providing a composition that contains a therapeutically effective amount of a medicament, said medicament being suitable for topical administration to a nail;
   (2) applying an etching effective amount of a chemical etching agent to the nail surface;
   (3) etching the surface of the nail in an amount sufficient to increase the surface of the nail at least 10% without breaching the surface of the nail by mechanically drilling a hole therethrough; and following the etching step;
   (4) applying the composition to the surface of the nail;
   wherein the chemical etching agent is about 20% tartaric acid or about 10% phosphoric acid or salts thereof.
2. The method of claim 1, wherein the medicament is an antifungal medicament.
3. The method of claim 1, wherein the composition is delivered to the nail bed transonychially and perionychially.
4. The method of claim 1, wherein the composition comprises at least one of a nail growth agent, nail hardening agent, nail softening agent, nail penetration enhancer, antimicrobial, antifungal, keratolytic agent or a bioadhesive agent.
5. The method of claim 1, wherein the composition is in the form of a gel.
6. The method of claim 1, wherein the composition is in the form of a liquid or a lacquer.
7. The method of claim 1, wherein the composition is in the form of a bioadhesive strip attachable to the nail or nail area.
8. The method of claim 1, wherein the etching step increases the surface area of the etched surface at least 20%.
9. The method of claim 2, wherein the antifungal medicament is selected from the group consisting of miconazole nitrate, ketoconazole, itraconazole, fluconazole, econazole, terconazole, saperconazole, amorolfine, ciclopirox, oxiconazole, clotrimazole, terbinafine, butenafine, and naftifine.
10. The method of claim 1, further comprising filing the nail to reduce thickness and/or alter the contour of the nail.
11. A method of treating a fungal infection of the fingernail or toenail, comprising:
    (1) providing a therapeutically effective amount of an antifungal medicament formulation;
    (2) etching the surface of a nail in an amount sufficient to increase the surface of the nail at least 10% without breaching the surface of the nail by mechanically drilling a hole therethrough with an about 20% tartaric acid composition or with an about 10% phosphoric acid composition; and following the etching step,
    (3) applying said antifungal medicament formulation to the surface of the nail.
12. The method of claim 11, wherein said medicament formulation comprises at least one of a nail growth agent, nail hardening agent, nail softening agent, nail penetration enhancer, keratolytic agent or a bioadhesive agent.
13. The method of claim 11, wherein the antifungal medicament is selected from the group consisting of miconazole nitrate, ketoconazole, itraconazole, fluconazole, econazole, terconazole, saperconazole, amorolfine, ciclopirox, oxiconazole, clotrimazole, terbinafine, butenafine, and naftifine.

* * * * *